United States Patent [19]

Manley et al.

[11] 4,267,728
[45] May 19, 1981

[54] APPARATUS FOR ANALYZING THE FORCES ACTING ON A HUMAN FOOT

[76] Inventors: Michael T. Manley, Heath Cottage, Tarrylaw, Swaanswyk Rd., Tokai; Edward G. Solomon, 5 Chester Ct., 202 High Level Rd., Sea Point, both of Cape Town, Cape Province, South Africa

[21] Appl. No.: 54,000

[22] Filed: Jul. 2, 1979

[30] Foreign Application Priority Data

Jul. 4, 1978 [GB] United Kingdom ............... 28740/78

[51] Int. Cl.³ .......................... A61B 5/10; G01M 19/00
[52] U.S. Cl. ....................................... 73/172; 128/779; 340/721
[58] Field of Search .......................... 73/172; 128/779; 340/721

[56] References Cited

U.S. PATENT DOCUMENTS

| | | | |
|---|---|---|---|
| 3,894,437 | 7/1975 | Hagy | 73/172 |
| 4,136,682 | 1/1979 | Pedotti | 73/172 |
| 4,195,643 | 1/1980 | Pratt | 128/779 |

FOREIGN PATENT DOCUMENTS 2517008  11/1975  Fed. Rep. of Germany ........ 73/172

*Primary Examiner*—S. Clement Swisher
*Attorney, Agent, or Firm*—Stevens, Davis, Miller & Mosher

[57] ABSTRACT

Apparatus for analyzing the force acting on the human foot comprises television cameras for photographing the gait of the subject and for photographing the plantar surface of his foot through a transparent platform. The platform comprises a plurality of beams each of which is supported at each end by means for detecting the load imposed on each beam. The video outputs of the two cameras and the load on each beam are displayed on a monitor screen. The apparatus also includes circuitry for determining from the loads on the ends of the beam where the center of pressure is on each beam. These centers of pressure are displayed superimposed on the image of the plantar surface.

10 Claims, 10 Drawing Figures

APPARATUS FOR ANALYZING THE FORCES ACTING ON A HUMAN FOOT

This invention relates to apparatus for analysing the forces acting on a human foot.

The object of the present invention is to provide apparatus which records the dynamic force distribution acting on the plantar surface of a foot during the stance phase of gait.

A further object of the invention is to provide apparatus which records and presents the force distribution information in such a way that it can readily be interpreted by medical personnel.

According to one aspect of the present invention there is provided apparatus for analysing the forces acting on a human foot, the apparatus comprising a platform composed of a plurality of transparent beams, each end of each beam being associated with means for measuring the load imposed on that end of the beam by a person who walks across the platform, a first television camera for photographing the gait of the subject, and a second television camera for photographing the plantar surface of the foot of the subject through the platform.

The apparatus can further include means for converting the output of the measuring means into a visual representation of the total force imposed on each beam and a further visual representation of the location of the centre of pressure on each beam. The visual representation of the centre of pressure on each beam can be displayed visually superimposed onto the image provided by said second camera.

The visual representation of the total force on each beam can be in the form of a bar-type display.

The apparatus can include a video recorder for recording the outputs of the two cameras, and for recording the signals representing the bar-type display and the centres of pressure.

The means for measuring the force imposed on each end of the beam can be foil type strain gauges mounted on mechanical elements that are deformed when the beams are loaded. The strain gauges can be bonded to respective cantilevers (which can be of stainless steel) which in turn support the ends of the beams.

According to a further aspect of the present invention there is provided a platform for use in the analysis of the forces imposed on a human foot during walking, the platform comprising a series of transparent beams, each end of each beam being associated with means for measuring the load imposed on that end of the beam by a person walking across the platform.

According to another aspect of the present invention there is provided a system comprising a visual display unit, means for photographing a sequence of events for display on said unit, measuring means for measuring at least one parameter associated with said sequence of events, and means for converting the output of the measuring means into an electronic signal thereby to permit display of the parameter as an electronically produced image superimposed on the display of the visual image.

According to a still further aspect of the present invention there is provided apparatus for indicating the relationship between two variables the sum of which varies, the apparatus comprising a ramp signal generating means, the rate of increase of the output of which depends on the magnitude of one input signal, and comparison means for determining when the output of the ramp signal generating means exceeds the magnitude of the other input signal.

According to yet another aspect of the present invention there is provided an analogue divider for providing a signal indicative of the quotient between two varying signals, the divider comprising a ramp signal generating means the rate of increase of the output of which depends on the magnitude of one input signal, and comparison means for determining when the output of the ramp signal generating means exceeds the magnitude of the other input signal.

The ramp signal generating means can be an integrator, and the comparison means can be a comparator.

According to yet a further aspect of the present invention there is provided a method of providing a signal indicative of the quotient between two variable signals, the method comprising generating a ramp signal the rate of increase of which depends on the magnitude of one input signal, and determining the time taken for the ramp signal to increase from zero to the magnitude of the second signal.

For a better understanding of the present invention, and to show how the same may be carried into effect, reference will now be made, by way of example, to the accompanying drawings in which:

FIG. 2b is a cross-section of the platform of FIG. 2a;

Figure 1:
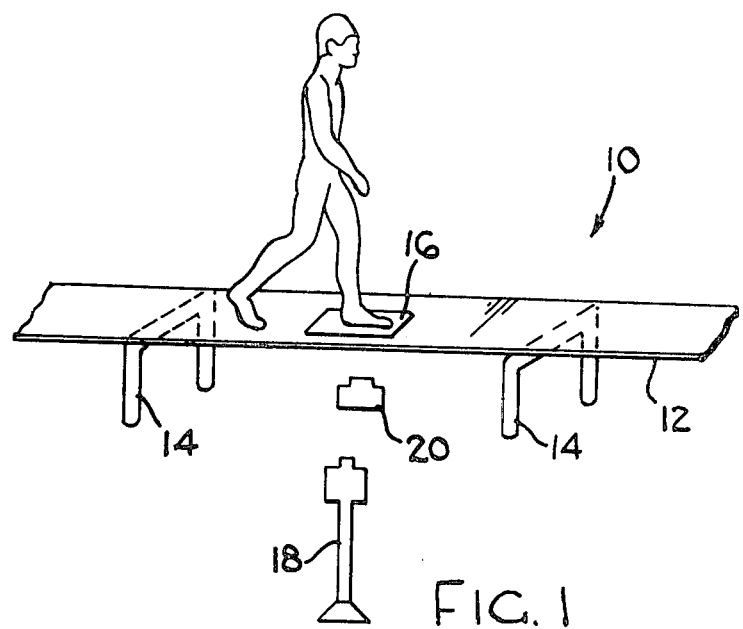
FIG. 1 is a diagrammatic representation of analysis apparatus in accordance with the present invention.
Figure 2A:
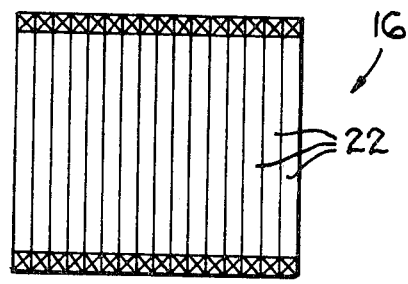
FIG. 2a is a plan view of a platform of the apparatus.
Figure 2B:
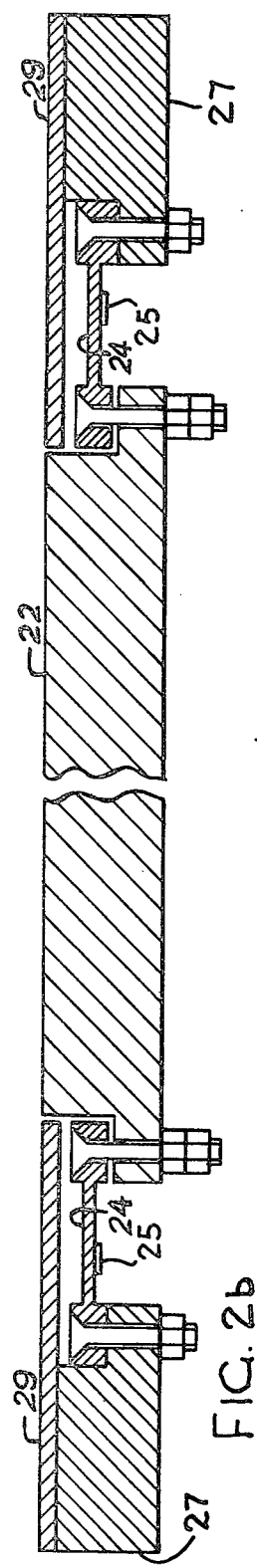

Referring firstly to FIG. 1, the apparatus illustrated is generally referenced 10 and comprises a raised walkway 12 supported on arches 14. A platform 16 (shown in more detail in FIG. 2) forms part of the walkway 12. A first television camera 18 which is horizontally positioned is provided alongside the walkway 12 and a second television camera 20, which is vertically positioned, is located beneath the platform 16. The camera 18 records the gait of a person walking along the walkway and the camera 20 photographs the plantar surface of the foot during its contact with the platform.

The camera 18 can, if desired, be located at the forward or rearward end of the walkway so as to photograph the gait of the subject as seen from the front or rear. Furthermore, the camera 20 can be located to one side of the walkway and there can be an inclined mirror below the walkway for reflecting to the camera the image of the plantar surface.

The platform 16 (see particularly FIGS. 2a and 2b) comprises sixteen transparent beams 22 arranged transversely of the walkway. Each end of each beam is supported by a stainless steel cantilever 24, there being a foil type strain gauge 25 bonded to each cantilever 24. The cantilevers 24 are mounted on a frame 27 of the platform and a cover plate 29 conceals and protects the construction. It will be understood that each strain gauge reflects the degree of deflection of the associated cantilever which in turn is a measure of the load imposed thereon.

The construction of the supports of the beams enables not only the total vertical force on the platform to be determined but also enables the position of the centre of pressure on each beam to be located.

The output from each strain gauge is fed to a multiplexed amplifier which incorporates an automatic bridge balancing circuit which, when activated, drives a digital to analogue converter so that the amplifier output goes to zero. The 16-bit digital word required to produce this zero output for each channel is stored in a random access memory. Before use of the apparatus, each channel is selected in turn and zeroed.

Due to mechanical tolerances in the construction of the cantilevers and positioning of the strain gauges, the force transducers have slightly differing sensitivities. For this reason it is necessary to include a digitally programmable gain stage in the amplifier. Each channel has its own 6-bit gain factor which is stored in a CMOS memory which has a standby battery to maintain this data when the instrument is turned off. Alternatively, this data can be permanently stored in a read only memory obviating the need for the stand by battery.

During measurement, as each channel is selected, its associated 16-bit zeroing word and 6-bit gain factor are recalled from memory and used to offset and scale the output in order to produce a signal proportional to the force carried by that particular cantilever.

Figure 3:
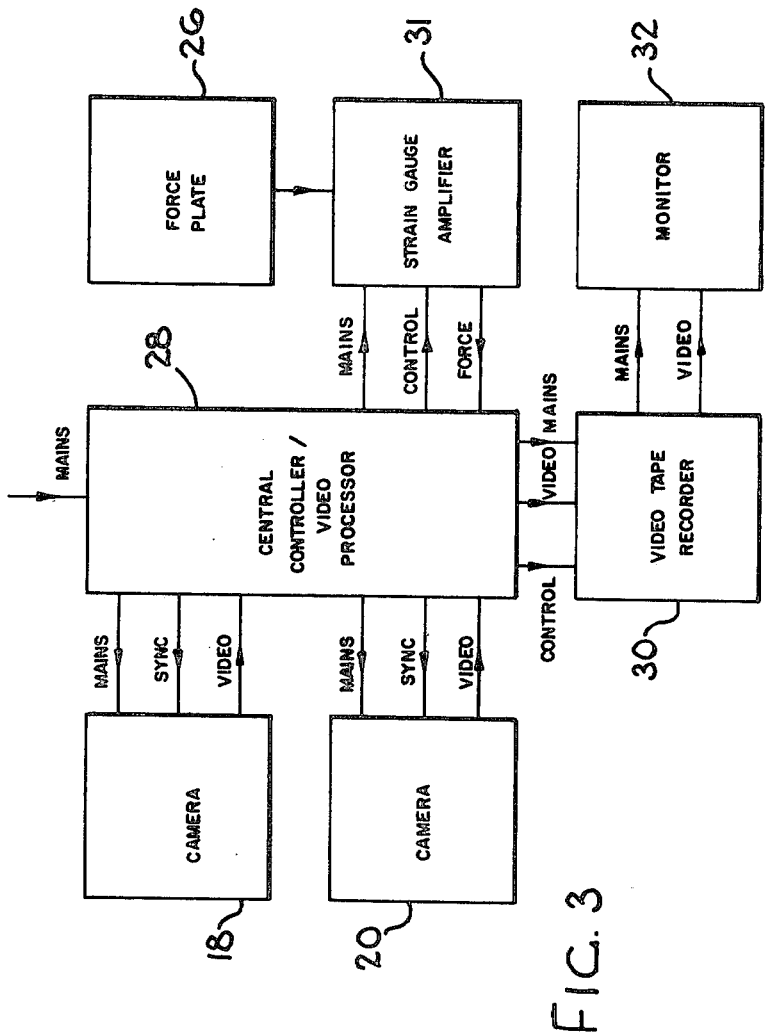
FIG. 3 is a block diagram of the electronic components of the apparatus.

The electronic system is illustrated in FIG. 3 where the television cameras are shown as blocks 18 and 20 and the group of strain gauges as block 26. The block 28 comprises a control unit capable of processing the signals from the strain gauges, synchronising the two television cameras and producing the electronically created, composite output images which are required. The block 31 represents the multiplexed strain gauge amplifier the output of which is fed to the block 28.

More detailed block diagrams of the multiplexed amplifier and of the unit 28 will be described hereinafter with reference to FIGS. 5 and 6.

Block 30 indicates a video recorder by means of which the output of the unit constituting the block 28 is stored for future analysis. To facilitate the analysis procedure, the video recorder preferably has a 'stills' facility to permit a 'frame by frame' analysis to be made subsequently. A television monitor for immediate display of the output of the unit is shown at 32.

The mains input to the system is to the unit from where it is distributed via its switched power outlets to the two cameras 18 and 20, strain gauge amplifier 31, video tape recorder 30 and monitor 32.

In addition to the power cable, there are two cables running to each of the cameras. One cable carries the synchronisation pulses to the camera and the other the video output from that camera.

The strain gauge amplifier 31 also has two signal cables, one to carry the control signals for the input multiplexer and bridge balancing circuitry, and the other to carry the amplifier output back to the unit 28.

There are two outputs from the unit 28 to the video tape recorder 30, one being to stop and start the VTR, and the other to carry the video signal to the VTR.

Figure 4:
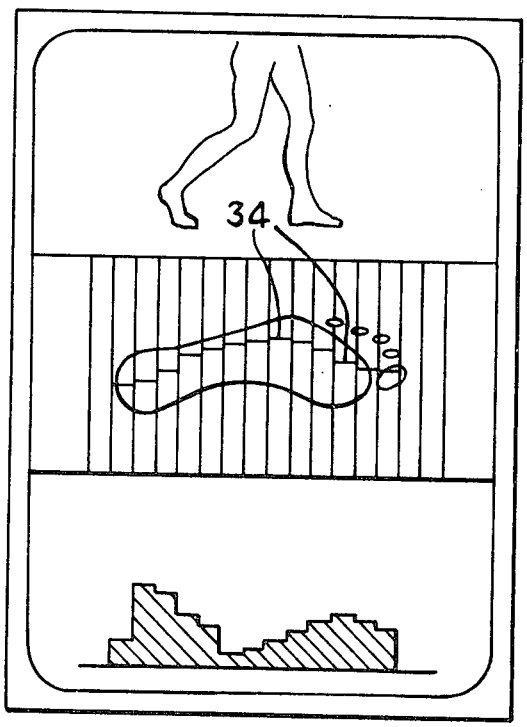
FIG. 4 illustrates the visual display of the apparatus.

Turning now to FIG. 4, a visual display screen is shown in this Figure, the screen being divided horizontally into three segments. It will be noted that the screen is 'on its side', scanning therefore being from bottom to top. The television camera 18 continuously records the gait of the subject and this is displayed in the upper segment of the horizontally divided screen. The image produced by the television camera 20 is displayed on the centre segment of the screen. The boundaries between adjacent beams 22 are also visible in this segment. Electronically superimposed on the image of the plantar surface are lines 34 each of which has a length equal to the width of one beam. These lines are created by comparing, for each beam, the outputs of its two force transducers and determining on the basis of this comparison where the centre of pressure is on each beam. The instantaneous centres of pressure are then displayed visually as the lines 34.

The lower segment of the screen displays the total force to which each beam is subjected, these total forces being displayed as a bar-type display which has the appearance of a histogram. The height of each bar represents the force on the related beam.

The multiplexed strain gauge amplifier (block 31) is required to be capable of energising the force transducers, of selecting a particular transducer and producing an output voltage which is directly proportional to the force exerted on that transducer.

In order to eliminate the tedious job of manually balancing each strain gauge bridge before use, the strain gauge amplifier incorporates an automatic bridge balancing circuit which, when activated, balances the selected channel. Thus before a test, with the force plate unloaded, each channel is selected and balanced. This selection and balancing routine is performed by the unit 28 as will be described.

In addition, as the force transducers have slightly different sensitivities, it is necessary to provide means for scaling each channel in order to standardise the output from each transducer.

Figure 5:
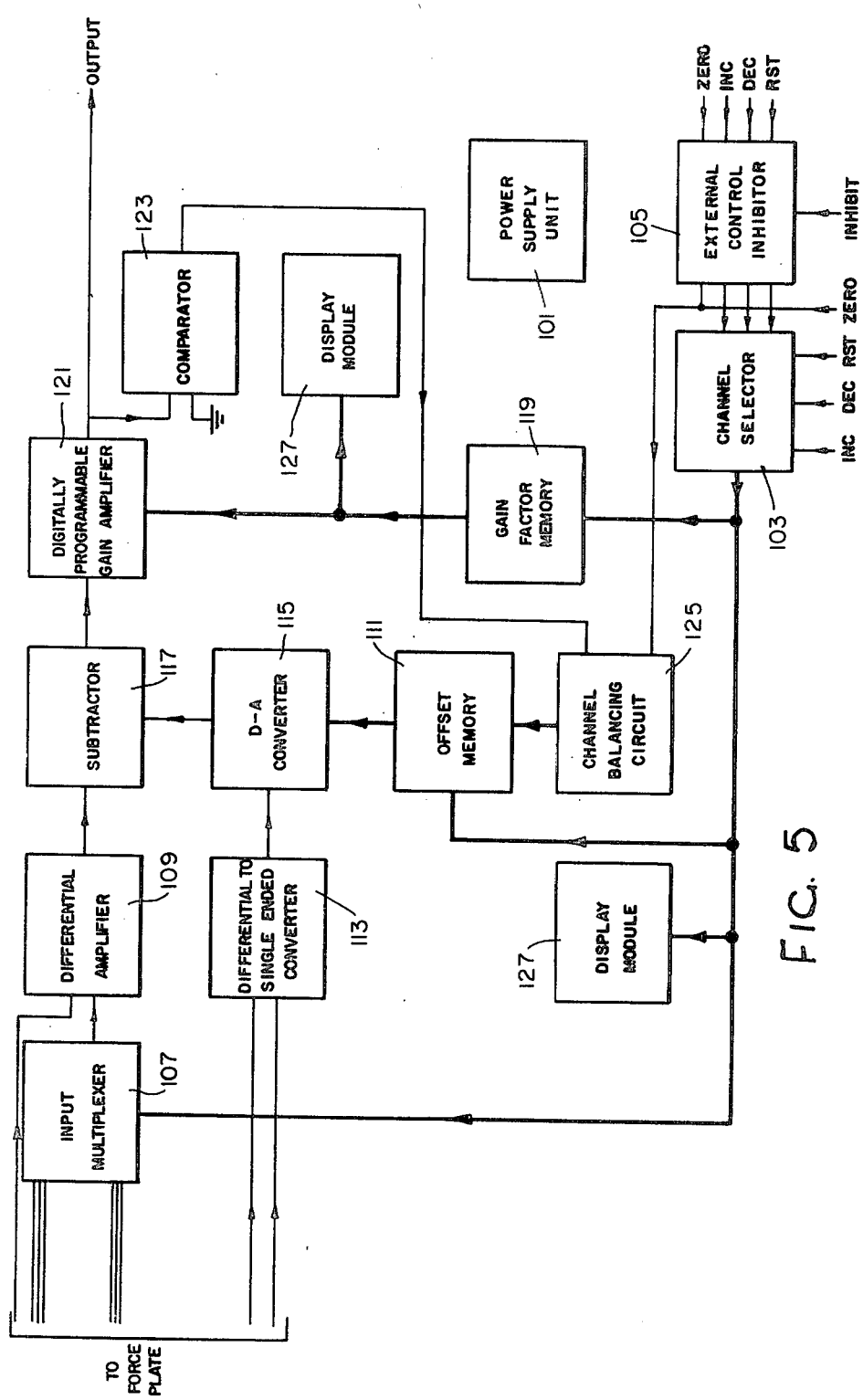
FIGS. 5 and 6 are block diagrams of a multiplexed amplifier and of a control unit.

The block diagram of the multiplexed strain gauge amplifier is shown in FIG. 5. The operation of the complete strain gauge amplifier will best be understood by considering each block in FIG. 5 in turn. The amplifier to be described has 64 channels. Only 32 of these are used and the remaining 32 are held in reserve to permit an increase in the number of beams to be accommodated.

The power supply unit 101 provides the necessary power for the electronics as well as a separate 5 V supply for the strain gauge force transducers.

The channel selector 103 is a 6-bit binary up/down counter which can be reset to zero, incremented or decremented.

The external control inhibitor 105 is used to disable all four external control inputs when the amplifier is to be used manually only. This facility is only used during calibration and during test routines, e.g., when fault finding.

The input multiplexer 107, under the control of the channel selector, feeds the output of the required force transducer to the input of the differential amplifier 109.

The differential amplifier 109 amplifies the output from the selected force transducer.

The offset memory 111 is a 64×16 bit random access memory which contains a digitally stored voltage for each channel which corresponds to the offset from that channel's force transducer.

The differential to single ended converter 113 senses the strain gauge bridge energizing voltage at the force plate and converts it to a ground referenced potential which is used as the reference for the D-A converter.

The D-A converter 115 produces an output voltage digitally stored in the offset memory which corresponds to the offset from the selected force transducer.

The subtractor subtracts 117 the output of the D-A converter from the differential amplifier output.

The gain factor memory 119 is a 64×6 bit read only memory which contains a scaling factor for each channel to standardize the outputs from the force transducers.

The digitally programmable gain amplifier 121, under the control of the gain factor memory, scales the output from the selected force transducer to a standard sensitivity.

The comparator 123 senses the output voltage and produces a single bit output whose state depends on whether the output voltage is positive or negative.

The channel balancing circuit 125 is a 16-bit successive approximation register which zeros the amplifier output by driving the D-A converter to produce a voltage equal to the output of the differential amplifier. The 16 bit word required to do this is stored in the offset memory 111.

The display modules 127 accept a 6-bit binary input and produce a corresponding two digit display. Two of these units are used, one to display the number of the channel selected and the other to display the gain factor of that channel. This facility is only activated during manual operation.

The central controller/video processor (block 28) is required to perform a number of different functions, namely (1) synchronise the two television cameras 18 and 20
(2) synchronize the input multiplexer 107 of the strain gauge amplifier
(3) accept the video outputs of the television cameras 18 and 20
(4) accept the output of the strain gauge amplifier and compute the total vertical force and position of the centre of pressure for each force plate beam
(5) generate the composite video picture
(6) balance all the channels of the strain gauge amplifier and put the video tape recorder 30 into the record mode at the start of a measurement cycle
(7) stop the video tape recorder 30 at the end of a measurement cycle.

Figure 6:
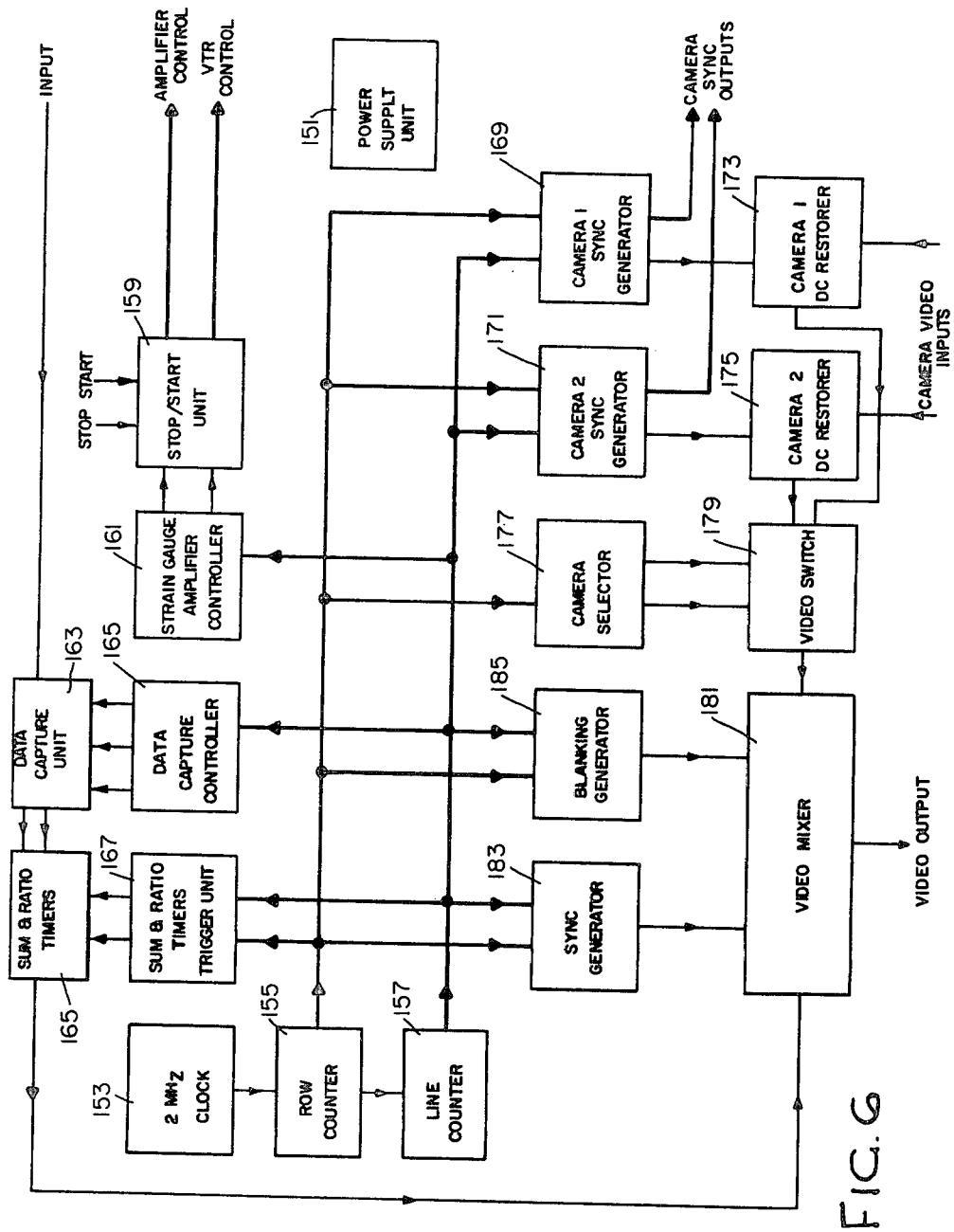

The operation of the central unit 28 will best be understood by considering each block in FIG. 6 in turn.

The power supply unit 151 produces the necessary supply voltages for all the circuitry of the central controller/video processor.

The 2 MHz clock 153 is a crystal controlled oscillator which is the master timing reference for the entire system.

The row counter 155 is a 7-bit binary counter which divides the 2 MHz clock frequency by 128 to give the required 15,625 Hz line frequency. The 7-bit output uniquely defines any ½ μsec period in a line.

The line counter 157 is a 9-bit binary counter arranged as a divide-by-312 stage. The 9-bit output uniquely defines any line in a video field.

The stop/start unit 159 sequentially selects each of the strain gauge amplifier channels and balances it at the start of a measurement cycle as well as putting the video tape recorder into the record mode. At the end of the measurement cycle it stops the video tape recorder.

The strain gauge amplifier controller 161 controls the input multiplexer 107 of the strain gauge amplifier and thus determines which force transducer is to be sampled.

The data capture unit 163 stores the values of the forces as measured sequentially by the multiplexed strain gauge amplifier and outputs these stored values in pairs to the sum and ratio timers 165. The two values outputted correspond to the forces at each end of a given beam.

The data capture controller 165 controls the storing of samples from the strain gauge amplifier as well as the outputting of these stored samples to the sum and ratio timers.

The sum and ratio timers 165 use the forces, measured by the strain gauge amplifier and stored in the data capture unit, to generate the bar chart and centre of pressure lines respectively.

The sum and ratio timers trigger unit 167 triggers these timers at the correct instants.

The camera sync generators 169, 171 produce the necessary line and field sync pulses to synchronise their respective cameras with the row and line counters. Each sync generator also produces a short pulse at some time during the black level output of its associated camera for DC restoration purposes.

The DC restorers 173, 175 adjust the DC level of the video signals from the cameras so that black level corresponds to 0V output.

The camera selector 177 determines which, if any, of the two camera outputs is to be selected for display on the monitor at any instant.

The video switch 179, under the control of the camera selector, feeds the video signal from camera 1 or camera 2, or no video signal at all to the video mixer 181.

The sync generator 183 produces a digital sync waveform.

The blanking generator 185 produces a digital blanking waveform.

The video mixer 181 combines the outputs from the sync generator, blanking generator, video switch and sum and ratio timers to produce the required composite video output.

Figure 7:
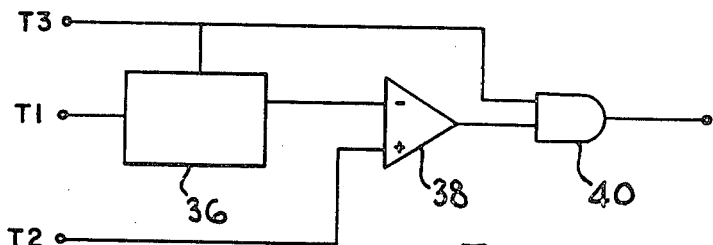
FIG. 7 is a block diagram of a voltage ratio to period convertor.
Figure 8:
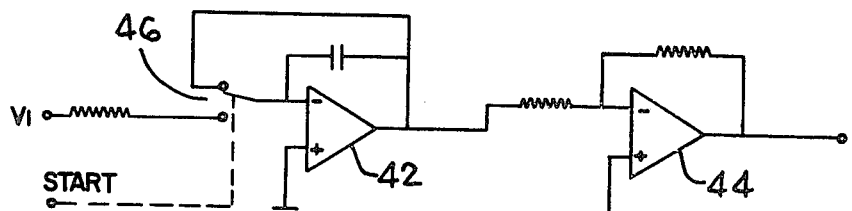
FIG. 8 is a circuit diagram of an integrator which constitutes a voltage controlled ramp generator for the convertor illustrated in FIG. 7.

The circuit which enables the centres of pressure to be displayed as shown in the lower segment of FIG. 4 is illustrated in FIGS. 7 and 8. This circuit forms part of the 'sum and ratio' timers block in FIG. 6. Referring firstly to FIG. 7, reference numeral 36 designates a voltage controlled ramp generator, 38 designates a comparator, and 40 an AND gate. The voltages V1 and V2 applied to the input terminals T1 and T2 are derived from the force transducer outputs and a START input is applied to terminal T3.

Figure 9:
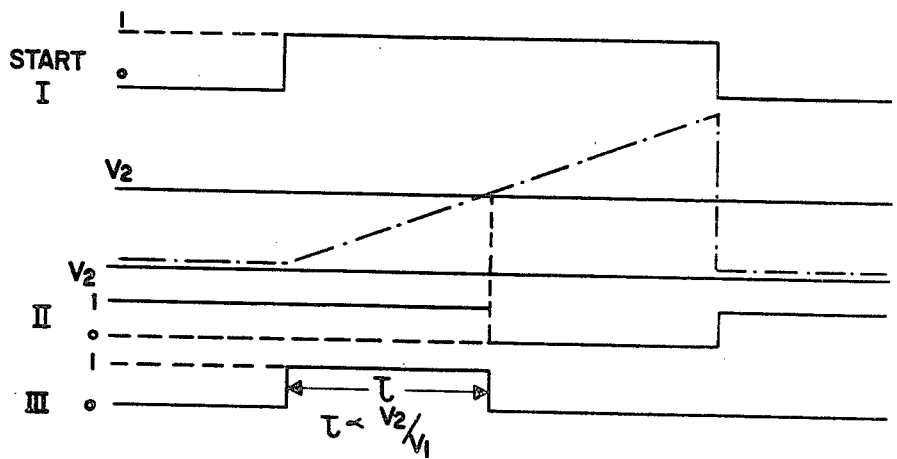
FIG. 9 illustrates some wave forms.

A possible construction of the ramp generator is shown in FIG. 8 and the wave forms of the START input, the comparator output and the AND gate output are shown at I, II and III in FIG. 9.

In FIG. 8 the reference numerals 42 and 44 indicate amplifiers and the reference numeral 46 indicates a single pole, double throw switch.

As the START input goes to a logical high, the ramp generator output voltage begins to rise at a rate proportional to voltage V1. When the ramp generator output voltage exceeds input voltage V2 the comparator output goes to a logical low. The comparator output is gated with the START signal. The AND gate output is then at a logical high for a period proportional to the voltage ratio V2/V1.

The voltage V2 is proportional to the force on one end of the beam and the voltage V1 is proportional to the total force on the beam. Thus the ratio V1:V2 is an indication of the location of the centre of pressure. The circuit illustrated uses this ratio to control the electron beam so that the lines 34 are correctly positioned on the screen.

It will be understood that if greater resolution is required then the number of beams can be increased and their width decreased so that a normal sized foot will span more beams than is illustrated in the centre segment of FIG. 4.

As an aid to analysis, it is possible to produce (either electronically or by cinephotography of the television screen) a slow motion film of the output data.

The platform 16 can be replaced by a one piece platform of transparent material supported by an array of force transducers which enable some or all of the following parameters to be measured:

(i) the three components of any force imposed thereon;

(ii) the co-ordinates of the instantaneous centre of pressure;

(iii) the moment about an axis normal to the platform.

The camera 20 can be provided in conjunction with this platform so as to photograph the plantar surface. This visual image can be displayed with one or more electronically created images superimposed thereon, these images being derived from the output of the force transducers. For example, the instantaneous center of pressure on the platform can be displayed as a point superimposed on the image of the plantar surface. Slow motion facilities can be used in this connection to permit evaluation. It is also possible to use the image of the camera 18 with an electronically created image superimposed on it. For example, the visual image may have an image representing the moment superimposed thereon. The electronic images can, where appropriate, be in the form of bar-type displays.

The video system of the apparatus described is based upon a conventional 625 line system having two interlaced fields per picture and twenty five pictures per second. The line frequency of such a conventional system is $625 \times 25 = 15,625$ Hz and the field frequency of such a conventional system is $2 \times 25 = 50$ Hz.

Since the optical resolution requirements of the apparatus are low and since the video tape recorder displays a field and not a picture (two fields), at least during stop motion playback, it was decided in developing the apparatus that the synchronisation circuitry could be greatly simplified by using a non-interlaced video system without adversely affecting picture quality. The video system of the apparatus is therefore a 624 line system (312 lines per field) having the same 15,625 Hz line frequency but a slightly different field frequency of $15,625 \div 312 = 50.08$ Hz.

It has been found that this gives rise to a problem when trying to obtain a still picture from the video recorder as picture roll and line tearing are encountered. Consequently, even though the synchronisation circuitry is more complicated, a 2:1 interlaced system is to be preferred over the non-interlaced system as it eliminates these difficulties with the still pictures.

We claim:

1. An apparatus for analyzing the forces acting on a foot comprising:
   a platform composed of a plurality of transparent beams,
   each end of each beam being associated with means for measuring a load imposed on that end of the beam by a subject walking across said platform;
   a first television camera for providing a first video image of the gait of said subject;
   a second television camera for providing a second video image of the plantar surface of the foot of said subject as viewed through said platform;
   means for converting the output of said measuring means to a visual display signal representative of the force acting on the foot of a subject walking across said platform; and,
   means for simultaneously displaying said first and second video images and said force representative visual display signal.

2. An apparatus according to claim 1 wherein said converting means converts the output of the measuring means into a first visual display signal representative of the total force imposed on each beam and a second visual display signal representative of the location of the center of pressure on each beam and said display means displays said first and second visual display signals.

3. An apparatus according to claim 2 wherein said display means displays said first and second video images and said first and second force representative visual display signals on a common display device.

4. An apparatus according to claim 2 wherein said display means displays said second visual display signal superimposed on said second video image.

5. An apparatus according to claim 1 further comprising a video recorder connected to record the outputs of said first and second cameras, and to record signals representing said first and second visual display signals.

6. An apparatus according to claims 2, 3 or 4 wherein said first visual display signal provided by said converting means is a bar-type display of the total force on each beam.

7. An apparatus according to claim 1, wherein the load measuring means comprises foil type strain gauges mounted on mechanical elements that are deformed when the beams are loaded.

8. An apparatus according to claim 7, wherein said strain gauges are bonded to respective cantilevers which in turn support the ends of the beams.

9. An apparatus according to claim 2 wherein said converting means includes a ramp signal generating means, the rate of increase of the output of which depends on the magnitude of a first voltage signal corresponding to the force generated on one end of a measured beam, and comparison means for determining when the output of the ramp signal generating means exceeds the magnitude of a second voltage signal corresponding to the total force applied to a measured beam, the output of said comparator controlling generation of said second visual display signal.

10. An apparatus according to claim 9, wherein said ramp signal generating means is an integrator, and the comparison means is a comparator.

* * * * *